US009759645B2

(12) United States Patent
Rowe et al.

(10) Patent No.: US 9,759,645 B2
(45) Date of Patent: Sep. 12, 2017

(54) SWEEP EFFICIENCY FOR HOLE CLEANING

(71) Applicant: HALLIBURTON ENERGY SERVICES, INC., Houston, TX (US)

(72) Inventors: Mathew Dennis Rowe, Lafayette, LA (US); Walter Varney Andrew Graves, Lafayette, LA (US); Clinton Cheramie Galliano, Houma, LA (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 0 days.

(21) Appl. No.: 15/118,973

(22) PCT Filed: Dec. 29, 2014

(86) PCT No.: PCT/US2014/072491
§ 371 (c)(1),
(2) Date: Aug. 15, 2016

(87) PCT Pub. No.: WO2016/108810
PCT Pub. Date: Jul. 7, 2016

(65) Prior Publication Data
US 2017/0052101 A1 Feb. 23, 2017

(51) Int. Cl.
*G01N 15/02* (2006.01)
*E21B 47/00* (2012.01)
(Continued)

(52) U.S. Cl.
CPC ............. *G01N 15/02* (2013.01); *E21B 21/08* (2013.01); *E21B 37/00* (2013.01); *E21B 47/00* (2013.01); *E21B 47/12* (2013.01); *G01N 15/06* (2013.01)

(58) Field of Classification Search
None
See application file for complete search history.

(56) References Cited

U.S. PATENT DOCUMENTS 4,413,511 A 11/1983 Godbey et al.
6,241,007 B1 6/2001 Kitahara et al.
(Continued)

OTHER PUBLICATIONS

International Patent Application No. PCT/US2014/072491, International Search Report and Written Opinion, mailed Aug. 27, 2015, 9 pages.

*Primary Examiner* — Paul West
*Assistant Examiner* — Mark A Shabman
(74) *Attorney, Agent, or Firm* — Kilpatrick Townsend & Stockton LLP

(57) ABSTRACT

Systems, computer readable medium, program code, and methods are provided for monitoring micro-electro-mechanical ("MEM") devices removed from a wellbore by a fluid flow stream. The system can include a first MEM reader and a second MEM reader. The first MEM reader can be positionable near the fluid flow stream for detecting MEM devices entering the wellbore in a fluid flow stream. The second MEM reader can be positionable near the fluid flow stream for detecting MEM devices exiting the wellbore in the fluid flow stream. The second MEM reader can detect MEM devices exiting the wellbore in a subsequent fluid flow stream. The system can further include a computing device for determining an amount and types of MEM devices remaining in the wellbore from the first fluid flow stream and an amount and types of MEM devices removed from the well-bore by the subsequent fluid flow stream.

20 Claims, 6 Drawing Sheets

(51) Int. Cl.
*E21B 21/08* (2006.01)
*E21B 37/00* (2006.01)
*E21B 47/12* (2012.01)
*G01N 15/06* (2006.01)

(56) References Cited

U.S. PATENT DOCUMENTS

| | | | |
|---|---|---|---|
| 6,281,489 B1 | 8/2001 | Tubel et al. | |
| 6,324,904 B1 * | 12/2001 | Ishikawa | E21B 47/011 |
| | | | 257/E29.022 |
| 6,357,536 B1 | 3/2002 | Schrader et al. | |
| 6,745,833 B2 * | 6/2004 | Aronstam | E21B 47/12 |
| | | | 166/250.11 |
| 6,935,425 B2 * | 8/2005 | Aronstam | E21B 47/12 |
| | | | 166/250.11 |
| 6,986,396 B2 | 1/2006 | Hemphill | |
| 7,455,108 B2 * | 11/2008 | Jenkins | E21B 47/12 |
| | | | 166/250.01 |
| 7,712,527 B2 | 5/2010 | Roddy | |
| 8,083,849 B2 * | 12/2011 | Lewis | G06F 3/1205 |
| | | | 106/606 |
| 8,162,050 B2 * | 4/2012 | Roddy | E21B 33/13 |
| | | | 166/250.14 |
| 8,269,648 B2 * | 9/2012 | Benischek | E21B 47/121 |
| | | | 340/853.1 |
| 8,584,519 B2 | 11/2013 | Maida et al. | |
| 8,800,651 B2 | 8/2014 | Fripp et al. | |
| 2008/0007421 A1 * | 1/2008 | Liu | G01V 11/002 |
| | | | 340/853.3 |
| 2009/0087912 A1 | 4/2009 | Ramos et al. | |
| 2009/0294174 A1 | 12/2009 | Harmer et al. | |
| 2010/0051266 A1 * | 3/2010 | Roddy | E21B 33/13 |
| | | | 166/250.01 |
| 2010/0139386 A1 * | 6/2010 | Taylor | E21B 47/1015 |
| | | | 73/152.23 |
| 2010/0274546 A1 | 10/2010 | Zafari et al. | |
| 2011/0191028 A1 | 8/2011 | Ross et al. | |
| 2011/0253373 A1 | 10/2011 | Kumar et al. | |
| 2011/0277996 A1 * | 11/2011 | Cullick | E21B 33/138 |
| | | | 166/250.12 |
| 2013/0054146 A1 | 2/2013 | Rasmus et al. | |
| 2013/0062068 A1 * | 3/2013 | Roddy | E21B 33/13 |
| | | | 166/310 |
| 2013/0118733 A1 | 5/2013 | Kumar | |
| 2013/0213647 A1 * | 8/2013 | Roddy | E21B 47/01 |
| | | | 166/255.1 |

* cited by examiner

SWEEP EFFICIENCY FOR HOLE CLEANING

CROSS-REFERENCE TO RELATED APPLICATIONS

This is a U.S. national phase under 35 U.S.C. 371 of International Patent Application No. PCT/US2014/072491, titled "Sweep Efficiency for Hole Cleaning" and filed Dec. 29, 2014, the entirety of which is incorporated herein by reference.

TECHNICAL FIELD

The present disclosure relates generally to determining or monitoring efficiency of using a fluid, for use in well systems, for wellbore cleaning. More specifically, but not by way of limitation, this disclosure relates to monitoring micro-electro-mechanical ("MEM") devices removed from a wellbore after a sweep is circulated through the wellbore and exits the wellbore.

BACKGROUND

A well system (e.g., oil or gas wells for extracting fluids from a subterranean formation) can include a drilling rig for drilling in a wellbore, along with other components or equipment. During drilling operations, well treatment or circulation fluid (e.g., a sweep, a pill or a slug) can circulate through the wellbore and can be used to sweep non-desirable solids from the wellbore to a surface of the wellbore. Effective sweep fluid selection and efficiently sweeping non-desirable solids from the wellbore can enhance the success of drilling operations and can help maintain high-quality sweep fluid properties.

DETAILED DESCRIPTION

Figure 1:
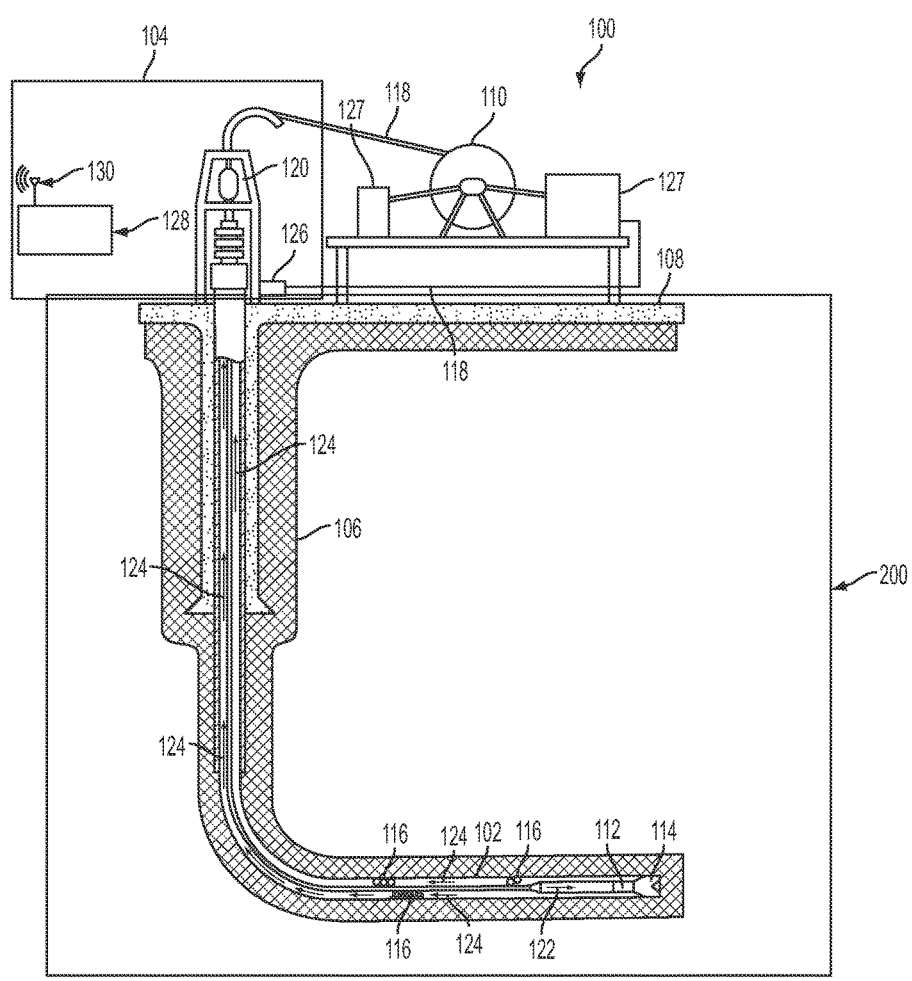
FIG. 1 is a schematic diagram showing a drilling rig on a wellbore along with a system for monitoring removal of micro-electro-mechanical ("MEM") devices representative of non-desirable solids according to one example of the present disclosure.

Certain aspects and features of the present disclosure are directed to monitoring micro-electro-mechanical ("MEM") devices swept from a wellbore and returned to a surface of the wellbore by a fluid flow stream. During drill rig operations, well treatment or circulation fluid (e.g., a sweep, a pill, or a slug) can circulate through the wellbore. The fluid may have rheological or density properties that can allow the fluid to suspend and lift non-desirable solids (e.g., sand, rock cuttings, or other debris) in the circulation fluids. Circulating the fluid may lift non-desirable solids to a surface of the wellbore as the fluid circulates through the wellbore and back to the surface. The efficiency of using the fluid to remove non-desirable solids from a wellbore may be monitored using MEM readers and MEM devices of different sizes, shapes, and densities that can represent certain types of non-desirable solids in the wellbore. The efficiency of using the fluid to remove MEM devices of a size, shape, or density from a wellbore may be representative of the efficiency of using the fluid to remove non-desirable solids of the same amount and type as the MEM devices.

For example, a known quantity and known types of MEM devices (e.g., devices with radio frequency identification ("RFID") tags) of different sizes, shapes, and densities may be placed in a fluid for a wellbore prior to the fluid entering the wellbore. In other examples, an unknown quantity and unknown types of MEM devices can be used. A MEM reader (e.g., an RFID tag reader) can detect an amount and types of MEM devices in the fluid prior to the fluid with the MEM devices entering the wellbore. The MEM reader can transmit this data to a computing device. A second MEM reader can detect an amount and types of MEM devices in the fluid subsequent to the fluid with the MEM devices exiting the wellbore. The second MEM reader can transmit this data to the computing device. The computing device can compare the data about the amount and types of MEM devices in the fluid before entering the wellbore and after exiting the wellbore to determine an amount and types of MEM devices remaining in the wellbore after the fluid with the MEM devices exits the wellbore.

After the fluid with the MEM devices exits the wellbore, a subsequent fluid may be injected into the wellbore for removing any MEM devices remaining in the wellbore. The subsequent fluid may be well treatment or circulation fluid (e.g., a sweep, a pill or a slug). The second MEM reader can detect an amount and types of MEM devices in the subsequent fluid, after the subsequent fluid exits the wellbore. The second MEM reader can transmit this data to the computing device. The computing device can compare the data about the amount and types of MEM devices in the wellbore before the subsequent fluid enters the wellbore and the amount and types of MEM devices exiting the wellbore in the subsequent fluid. The computing device can use this comparison to determine an amount and types of MEM devices removed from the wellbore by the subsequent fluid. The computing device can also use this comparison to determine an amount and types of MEM devices remaining in the wellbore after the subsequent fluid exits the wellbore.

The computing device may also use this comparison to determine a sweep efficiency of using the subsequent fluid to remove an amount and types of MEM devices from the wellbore. In other examples, the computing device may determine the inefficiency of using the subsequent fluid to remove an amount and types of MEM devices. The computing device may compare the sweep efficiency of using the subsequent fluid to remove an amount and type of MEM devices from the wellbore to a threshold of expected efficiency for using the subsequent fluid.

The computing device can output data representing the efficiency of using the subsequent fluid to remove an amount and types of MEM devices. Based on the output, changes can be made to the properties (e.g., density, viscosity, etc.)

of a fluid to be injected into the wellbore in a subsequent circulation for removing any MEM devices remaining in the wellbore.

In some examples, the sizes, shapes, or densities of the MEM devices may be representative of the sizes, shapes, or densities of non-desirable solids in the wellbore. The efficiency of using a fluid to remove an amount and types of MEM devices from the wellbore may correspond to the efficiency of using the fluid to remove non-desirable solids of the same amount and types as the MEM devices.

Determining and monitoring the efficiency of using a fluid to remove non-desirable solids from a wellbore can enhance the success of drilling operations on directional, high-angle, or deviated-wellbores. For example, improved sweep efficiency may translate into less wear and tear on a drill bit and more efficient drilling operations. Also, effectively monitoring removal of non-desirable solids may help determine sweep fluid properties such as viscosity, volume, or density for improving sweep efficiency.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative examples but, like the illustrative examples, should not be used to limit the present disclosure.

FIG. 1 is a schematic diagram showing a drilling rig 100 and a wellbore 102 along with a system 104 for monitoring removal of MEM devices, representative of non-desirable solids, according to one example of the present disclosure. In this example, drilling rig 100 is depicted for use on a well system 200 (e.g., an oil or gas well for extracting fluids from a subterranean formation 106). The drilling rig 100 is used to create a hole or wellbore 102 in a surface 108. The drilling rig includes a pump 110, a drill string 112, and a drill bit 114. The pump 110 can pump a variety of fluids or wellbore compositions, such as well treatment or circulation fluid through the drill string 112. The drill string 112 can transmit the fluid to the drill bit 114 through which the fluid exits into the wellbore 102.

The wellbore 102 has been drilled from the surface 108 and through subterranean formation 106. The wellbore can be a vertical, directional, high angle or deviated wellbore. As the wellbore 102 is drilled, the drill bit 114 can cut into rocks or sediments in the wellbore 102 and create rock cuttings and non-desirable solids 116. While the drill bit 114 cuts into the wellbore 102, pump 110 may pump a fluid flow stream 118 into the wellbore 102. The fluid flow stream may enter the wellbore 102 through a fluid flow input 120 for the wellbore and flow along flow path 122. Pumping the fluid flow stream 118 into wellbore 102 may allow the fluid flow stream 118 to lift non-desirable solids 116 to the surface 108 and out of a fluid flow output 126 for the wellbore 102. The fluid flow stream 118 may flow toward the surface 108 along flow path 124. At the surface 108, the fluid may be processed using equipment 127 to maintain or modify the fluid's desired characteristics.

The system 104, according to some examples, may be used for monitoring removal of MEM device, representative of the non-desirable solids 116, from the wellbore.

The system 104, according to certain examples, can include, among other things, a computing device or processing module 128. The computing device 128 can be positioned at the surface 108, below ground, or offsite. The computing device 128 can include a communication device 130 for transmitting and receiving data. The computing device 128 may be used to determine and monitor the efficiency of using a fluid to remove non-desirable solids from a wellbore.

Figure 2:
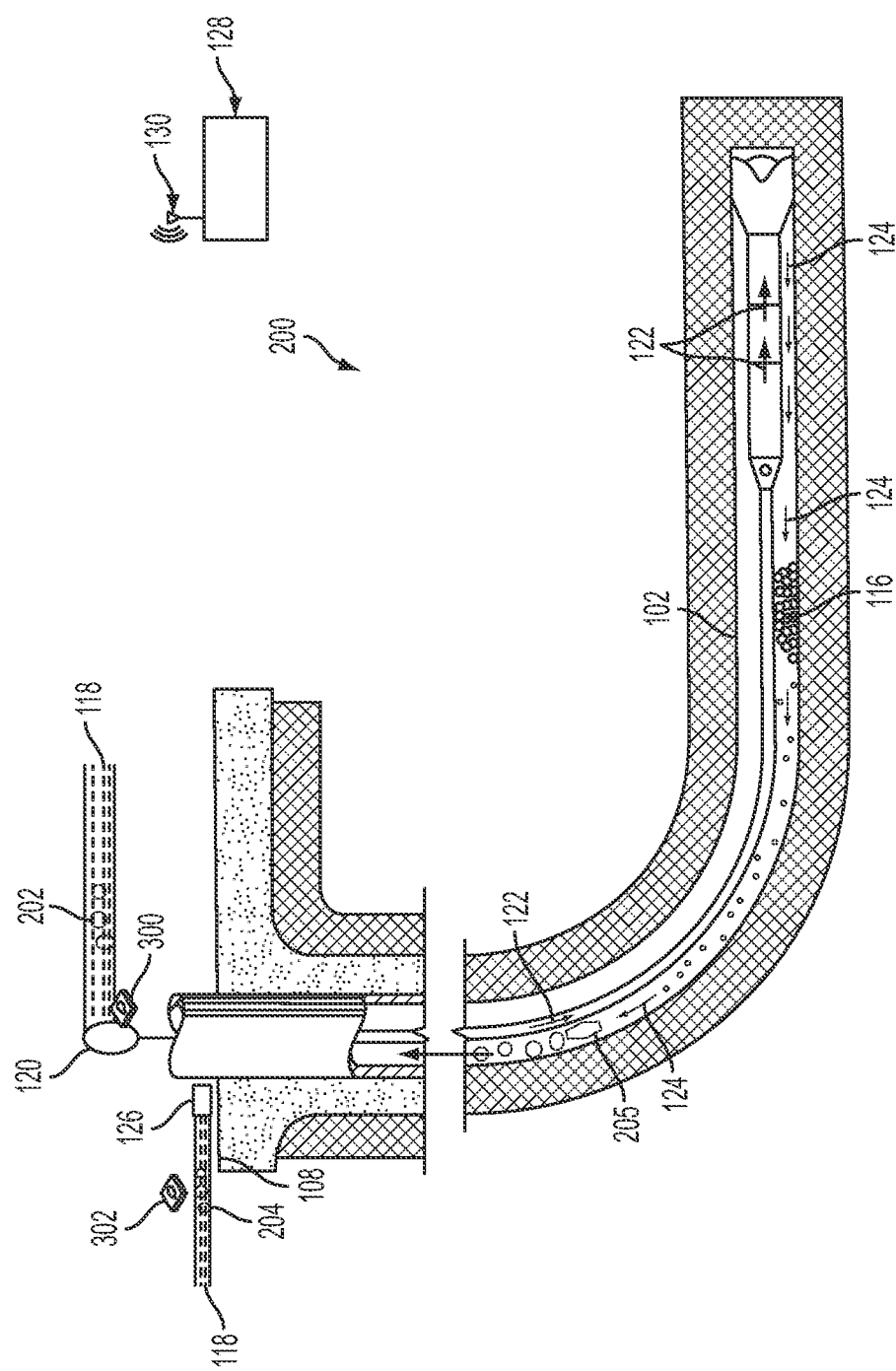
FIG. 2 is a schematic diagram showing a well system and two MEM readers, along with a computing device, according to another example of the present disclosure.

FIG. 2 is a schematic diagram of a well system 200, MEM devices 202, 204, 205, and two MEM readers 300, 302, along with a computing device 128 according to another example of the present disclosure. FIG. 2 depicts the well system 200 from a surface 108 and below.

The well system 200 may be any type of well system and may include a wellbore 102. The wellbore 102 may be a wellbore of any type of configuration. For example, the wellbore may be a vertical, a horizontal, or a deviated wellbore. The well system 200 can have a fluid flow input 120 for the wellbore and a fluid flow output 126 for the wellbore. The fluid flow input 120 can be near the wellbore 102 and may allow a fluid flow stream to enter into the wellbore 102. The fluid flow output 126 can be near the wellbore 102 and may allow a fluid flow stream to exit the wellbore near a surface 108. A fluid flow stream may flow into the wellbore along a flow path 122 and exit the wellbore along a flow path 124.

MEM devices 202, 204, 205 may be any micro-electromechanical devices disposable in a fluid flow stream for a wellbore. For example, the MEM devices can be devices with RFID tags. The MEM devices may also be different sizes, shapes, and densities. In some examples, the sizes, shapes, and densities of the MEM devices may be representative of the sizes, shapes, and densities of non-desirable solids 116 in a wellbore.

MEM readers 300, 302 can be any readers for detecting MEM devices (e.g., an RFID tag reader). The MEM readers 300, 302 may also detect an amount and type of MEM devices in a fluid flow stream.

A first MEM reader 300 may be positioned near a fluid flow stream 118 and a fluid flow input 120 for a wellbore 102. In some examples, the first MEM reader 300 may be positioned near the fluid flow stream 118 and between the wellbore 102 and the fluid flow input 120 for the wellbore 102. The first MEM reader 300 may detect MEM devices in the fluid flow stream 118 prior to the fluid flow input 120.

A second MEM reader 302 may be positioned near the fluid flow stream 118 and a fluid flow output 126 for the wellbore 102. The second MEM reader 302 may detect at least a subset of MEM devices in the fluid flow stream 118 subsequent to the fluid flow output 126.

In some examples, a known quantity and known types of MEM devices may be placed in the fluid flow stream 118 prior to the fluid flow stream 118 entering the fluid flow input 120. In other examples, an unknown quantity or unknown types of MEM devices can be used. The first MEM reader 300 may detect an amount and types of MEM devices 202 in the fluid flow stream 118 prior to the fluid flow stream 118 entering the fluid flow input 120. The fluid flow stream 118 may transport an amount and types of MEM devices toward a surface 108 and through a fluid flow output 126 as the fluid flow stream 118 flows along flow path 124. The second MEM reader 302 may detect an amount and types of MEM devices 204 in the fluid flow stream subsequent to the fluid flow stream exiting the fluid flow output 126. An amount and types of MEM devices 205 may remain in the wellbore after the fluid flow stream 118 exits the wellbore via the fluid flow output 126.

The first MEM reader 300 may detect individual MEM devices and store data that may be representative of a distribution of the amount and types of MEM devices of different sizes, shapes, and densities in the fluid flow stream

118 prior to the fluid flow stream entering 118 entering the fluid flow input 120. The distribution may correspond to the amount of each type of MEM device of a different size, shape, or density in the fluid flow stream 118 detected by the first MEM reader 300.

The second MEM reader 302 may detect individual MEM devices and store data that may be representative of a distribution of the amount and types of MEM devices of different sizes, shapes, and densities in the fluid flow stream 118 subsequent to the fluid flow stream exiting the fluid flow output 126. The distribution may correspond to the amount of each type of MEM device of a different size, shape, or density in the fluid flow stream 118 detected by the second MEM reader 302.

A computing device 128 may transmit to and receive data from the two MEM readers 300, 302. The first MEM reader 300 may transmit data to the computing device 128 via a communication device 130. The data may represent the amount and types of MEM devices 202 in the fluid flow stream 118 prior to the fluid flow stream 118 entering the fluid flow input 120. In other examples, the first MEM reader 300 may transmit other data that represents a distribution of the amount and types of MEM devices of different sizes, shapes, and densities in the fluid flow stream 118 prior to the fluid flow stream 118 entering the fluid flow input 120.

The second MEM reader 302 may transmit data to the computing device 128 via the communication device 130. The data may represent the amount and types of MEM devices 204 in the fluid flow stream 118 subsequent to the fluid flow stream 118 exiting the fluid flow output 126. In other examples, the second MEM reader 302 may transmit other data that represents a distribution of the amount and types of MEM devices of different sizes, shapes, and densities in the fluid flow stream 118 subsequent to the fluid flow stream 118 exiting the fluid flow output 126.

Figure 3:
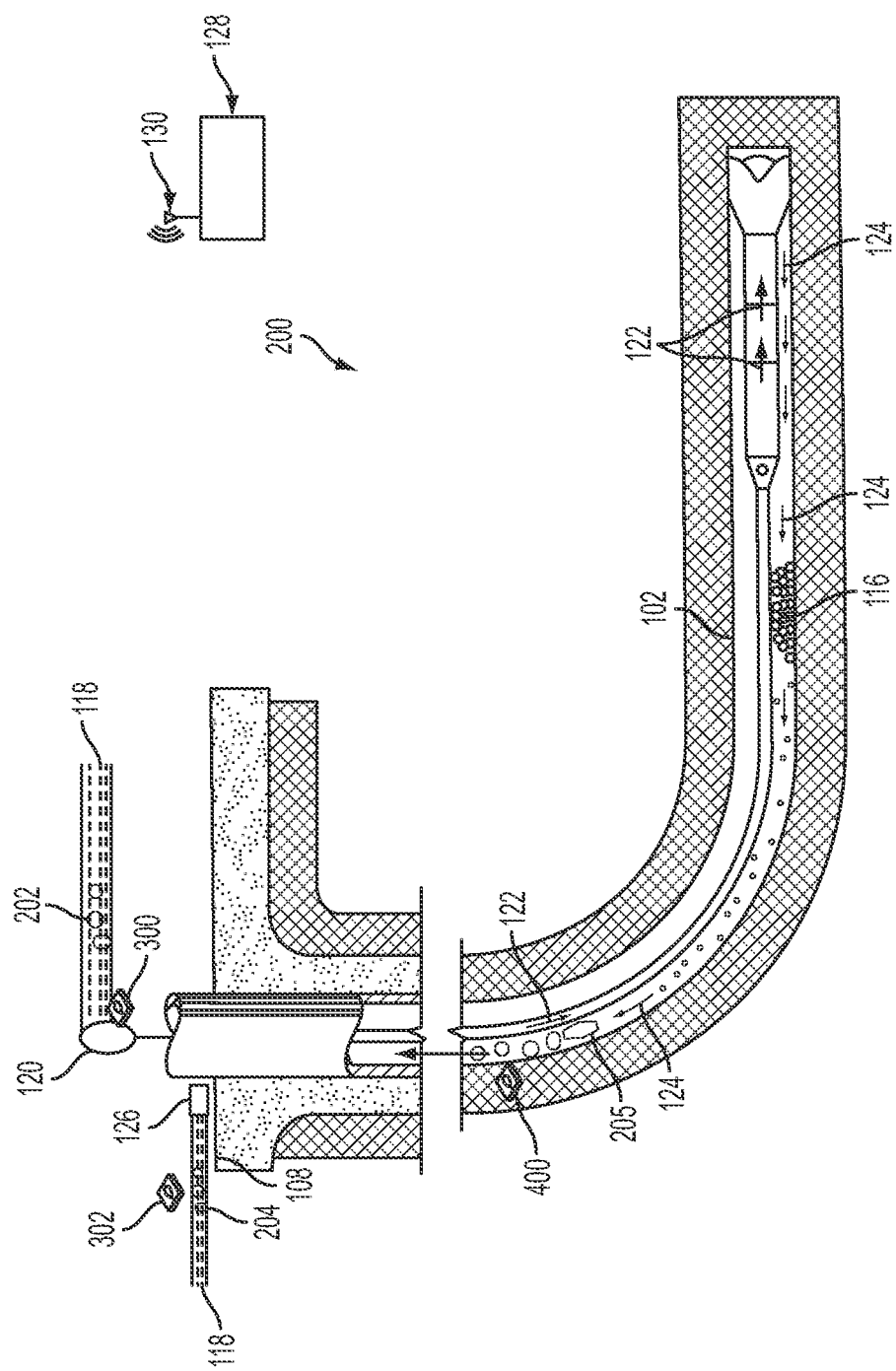
FIG. 3 is a schematic diagram showing a well system and three MEM readers, along with a computing device, according to another example of the present disclosure.

Other examples of a system for monitoring removal of MEM devices can use more than two MEM readers. For example, FIG. 3 is a schematic diagram of a well system 200, and three MEM readers along with a computing device according to another example of the present disclosure.

A first MEM reader 300 may detect an amount and types of MEM devices 202 in a fluid flow stream 118 prior to the fluid flow stream 118 entering a fluid flow input 120 for the wellbore 102. The first MEM reader 300 may transmit data to a computing device 128 via a communication device 130.

A second MEM reader 302 may detect an amount and types of MEM devices 204 in the fluid flow stream 118 subsequent to the fluid flow stream 118 exiting a fluid flow output for the wellbore 102. The second MEM reader 302 may transmit data to the computing device 128 via the communication device 130.

A third MEM reader 400 may be positioned near the fluid flow stream 118 and between the first MEM reader 300 and the second MEM reader 302. The third MEM reader 400 may detect at least a subset of MEM devices between the fluid flow input 120 and the fluid flow output 126. For example, the third MEM reader 400 may detect the MEM devices 205 remaining in the wellbore after the fluid flow stream 118 flows along flow path 124 and exits the wellbore 102. The third MEM reader 400 may transmit data to the computing device 128 via the communication device 130.

Figure 4:
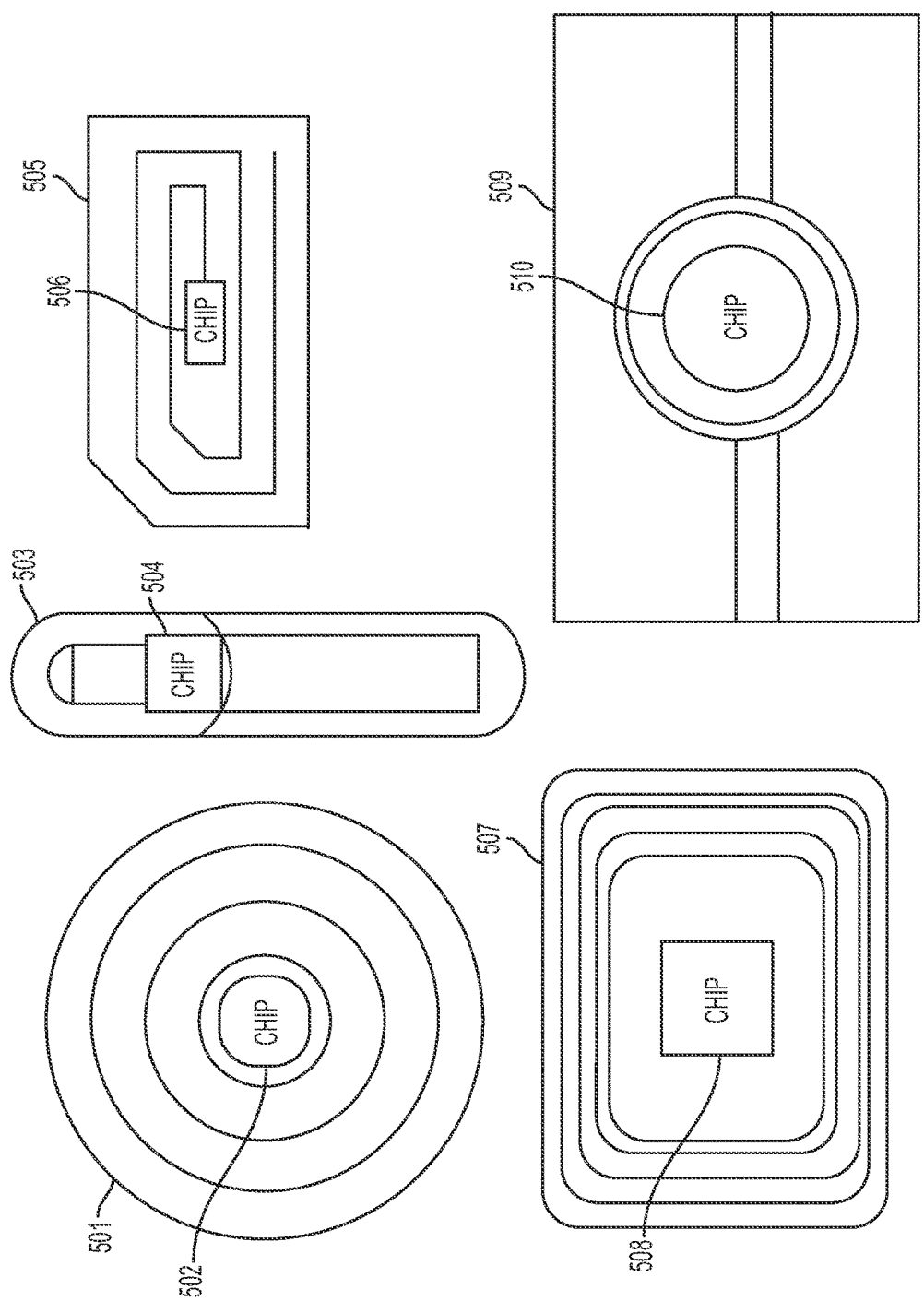
FIG. 4 is a schematic diagram showing a top view of MEM devices of different sizes and shapes according to one example of the present disclosure.

FIG. 4 is a perspective view of MEM devices of various sizes and shapes according to one example of the present disclosure, such as MEM devices that can be used with systems described previously.

In some examples, MEM devices used may be of any shape. The shape of the MEM devices may be representative of any shape of some non-desirable solids in the wellbore. The shape of a MEM device may refer to the external form, appearance or structure of the MEM device. For example, MEM device 501 has a shape that is generally circular or round and may be representative of non-desirable solids in a wellbore having a generally circular or round shape.

MEM devices used in some examples may be of any size. The size of a MEM device may be representative of any size of some non-desirable solids in the wellbore. The size of a MEM device may correspond to the dimensions of a shape of the MEM device. The size of a MEM device may be measured by the area, perimeter, circumference, diameter, length, cross section, or the like, of the shape of the MEM device. For example, the sizes of MEM devices 505, 507, 509 may be measured by the area or perimeter of the MEM devices' generally rectangular shapes. The MEM devices 505, 507, 509 may be representative of non-desirable solids in a wellbore having a generally rectangular shape and a similar perimeter, area, or size. In another example, the size of MEM device 503 may be measured by the length of the MEM device's generally cylindrical shape. The MEM device 503 may be representative of non-desirable solids in a wellbore having a generally cylindrical shape and a similar length.

The MEM devices may also be of any density. The density of a MEM device may be representative of a density of some non-desirable solids in the wellbore. The density of a MEM device may refer to the volumetric mass density or mass per unit volume of the MEM device. The density of a MEM device may depend on any number of factors including, without limitation, the size of the MEM device, the shape of the MEM device, the components of the MEM device, the material used for manufacturing the MEM device, and other factors. For example, a MEM device can have mechanical (e.g., levers, springs, vibrating structures, etc.), electrical (e.g., circuits, resistors, capacitors, inductors, etc.) and electro-mechanical components that range in size and affect the density of the MEM device. The MEM devices can also have sensors, actuators, and microelectronics. The MEM devices may also be manufactured from various materials, including, without limitation, silicon, polymers (e.g., poly(methyl methacrylate)), metals (e.g., copper, aluminum, titanium, etc.) ceramics, or other material, which may affect the density of the MEM device. For example, a MEM device manufactured using silicon may have a density of silicon (e.g., approximately 2.3 g/cm$^3$)

The sizes, shapes, or densities of the non-desirable solids that may be represented by the sizes, shapes, or densities of the MEM devices may be determined from solids or visual analysis of the wellbore conducted on-site or off-site.

The MEM devices 501, 503, 505, 507, 509 may include, or have components integrated onto, a microchip or chip 502, 504, 506, 508, 510, respectively, for storing data. For example, the MEM devices may be devices with RFID tags that use electromagnetic fields to transfer data that may be used to automatically identify and track the RFID tags. The MEM devices can also communicate with and be detected by MEM readers. In some examples, the MEM devices may communicate with and be detected by MEM readers within a proximity from the MEM devices.

Figure 5:
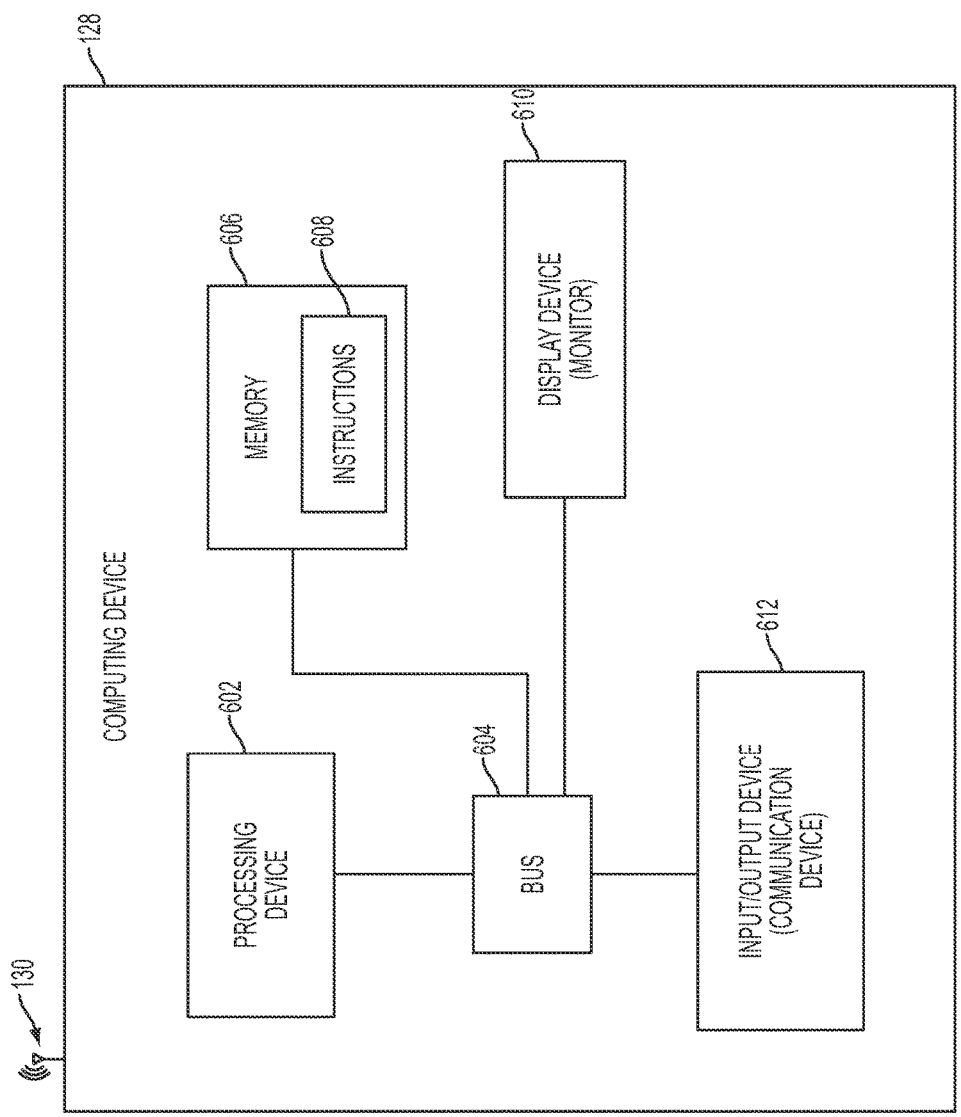
FIG. 5 is a block diagram showing a computing device for determining an amount and types of MEM devices remaining in a wellbore according to one example of the present disclosure.

FIG. 5 is a block diagram of a computing device 128 for determining an amount and types of MEM devices remaining in a wellbore after a fluid flow stream flows through the wellbore and exits the wellbore according to one example of the present disclosure.

The computing device 128 can include a processing device 602 interfaced with other hardware via a bus 604. The computing device 128 may also include a memory device 606. In some examples, the computing device 128 can include input/output interface components (e.g., a display device 610 and a communication device 612). The computing device 128 can also include other input/output interface components such as a key board, touch-sensitive surface, mouse, an alarm system and additional storage.

The computing device 128 can receive data from MEM readers via a communication device 130. In some examples, the communication device 130 can represent one or more of any components that facilitate a network connection. In some examples, the communication device may be wireless and can include wireless interfaces such as IEEE 802.11, Bluetooth, or radio interfaces for accessing cellular telephone networks (e.g., transceiver/antenna for accessing a CDMA, GSM, UMTS, or other mobile communications network). In another example, the communication device 130 can be wired and can include interfaces such as Ethernet, USB, IEEE 1394, or a fiber optic interface.

The processing device 602 can include one processing device or multiple processing devices. The processing device 602 can execute one or more efficiency operations for monitoring MEM devices removed from a wellbore by a fluid.

The processing device 602 can execute one or more efficiency operations for comparing an amount and types of MEM devices in a fluid flow stream prior to a fluid flow input for a wellbore and an amount and types of MEM devices in the fluid flow stream subsequent to a fluid flow output for the wellbore. The efficiency operations can be executed for using the comparison for determining an amount and types of the MEM devices remaining in the wellbore after the fluid flow stream with the MEM devices flows through the wellbore and exits the wellbore.

The processing device 602 can also execute efficiency operations for comparing the amount and types of the MEM devices remaining in the wellbore after the fluid flow stream with the MEM devices exits the wellbore and an amount and types of MEM devices in a subsequent fluid flow stream subsequent to the fluid flow output. The efficiency operations can also be executed for using the comparison for determining the amount and types of MEM devices removed from the wellbore by the subsequent fluid flow stream. The efficiency operations can also be executed for using the comparison to determine the amount and types of MEM devices remaining in the wellbore after the subsequent fluid flow stream exits the wellbore.

In another example, the processing device 602 can execute one or more efficiency operations for generating a distribution of the amount and types of MEM devices of different sizes, shapes, and densities in a fluid flow stream prior to the fluid flow input. The distribution may represent a number of MEM devices of each type of MEM device in the fluid flow stream prior to the fluid flow input. The processing device 602 can also execute efficiency operations for generating a distribution of the amount and types of MEM devices of different sizes, shapes, and densities in the fluid flow stream subsequent to the fluid flow output. The processing device 602 may also execute an efficiency operation for comparing the two distributions to determine the amount and types of MEM devices of different sizes, shapes, and densities remaining in the wellbore after the fluid flow stream with the MEM device flows through the wellbore and exits the wellbore.

The processing device 602 can also execute one or more efficiency operations for generating a distribution of the amount and types of MEM devices of different sizes, and densities in a subsequent fluid flow stream subsequent to the fluid flow output. The efficiency operations can be executed for comparing the amount and types of MEM devices of different sizes, shapes, and densities remaining in the wellbore after the first fluid flow stream with the MEM devices exits the wellbore and a distribution of the amount and types of MEM devices of different sizes, shapes, and densities in the subsequent fluid flow stream subsequent to the fluid flow output. The efficiency operations can be executed for using the comparison for determining or generating a distribution of the amount and types of MEM devices removed from the wellbore by the subsequent fluid flow stream. The distribution may represent an amount of each type of MEM device removed from the wellbore. The efficiency operations can also be executed for using the comparison for determining the amount of each type of MEM device remaining in the wellbore after the subsequent fluid flow stream exits the wellbore.

The efficiency operations may also be executed for using the comparison to determine the sweep efficiency of using the subsequent fluid to remove an amount and types of MEM devices from the wellbore. The efficiency operation may also be executed for determining a sweep efficiency rating for each type of MEM device removed from the wellbore by the subsequent fluid. The sweep efficiency rating may be representative of the efficiency of using the subsequent fluid to remove each type of MEM device. The efficiency operations may be executed for comparing the efficiency of using the subsequent fluid to remove an amount and types of MEM devices from the wellbore to a stored threshold of expected efficiency for using the subsequent fluid flow to remove MEM devise of an amount and different sizes, shapes, and densities. The processing device 602 can also execute efficiency operations for outputting this data.

The efficiency operations can also be executed for outputting the comparison or efficiency of using the subsequent fluid to remove an amount and types of MEM devices from the wellbore. The output can be used to determine properties (e.g., density, viscosity, etc.) of a fluid flow stream disposable in the wellbore for removing at least a subset of the amount and types of MEM devices of different sizes, shapes and densities, remaining in the wellbore after the second fluid flow stream exits the wellbore.

The efficiency operations can also be executed for analyzing the amount and types of MEM devices remaining in the wellbore after the second fluid flow stream exits the wellbore for determining properties of a fluid flow stream disposable in the wellbore for removing at least a subset of the amount and types of MEM devices remaining in the wellbore after the second fluid flow stream exits the wellbore.

In certain examples, the shapes, sizes, and densities of the MEM devices are representative of non-desirable solids in a wellbore to be removed by a fluid flow stream. The processing device 602 can execute an efficiency operation for determining an amount of MEM devices of a shape, size, or density, representative of the non-desirable solids, removed from wellbore by the fluid flow stream. The processing device may also execute an efficiency operation for determining the efficiency of using a fluid flow stream to remove non-desirable solids of the same size, shape, or density as the MEM devices removed from the wellbore by the fluid flow stream. The processing device may also execute an efficiency operation for determining the non-desirable solids of the same size, shape, or density as the MEM devices remaining in the wellbore.

The efficiency operations can also be executed for recognizing a threshold of expected efficiency for using a fluid flow stream to remove MEM devices of a shape, size, or density, representative of the non-desirable solids from the wellbore.

In some examples, the computing device 128 can also be communicatively coupled to a display device 610 via the bus 604. The display device can display data that may correspond to data received by the computing device 128 from a MEM reader. The display device may also display data that may correspond to data generated by executing an efficiency operation executed by the processing device 602.

The processing device 602 can also be communicatively coupled to a memory device 606 via the bus 604. The non-volatile memory device may include any type of memory that retains stored information when powered off. Non-limiting examples of the memory device 606 include EEPROM, flash memory, or any other type of non-volatile memory. In some examples, at least some of the memory device 606 can include a medium from which the processing device can read instructions 608. A computer-readable medium can include electronic, optical, magnetic, or other storage devices capable of providing the processing device 602 with computer-readable instructions or other program code. Non-limiting examples of a computer-readable medium include, but are not limited to, magnetic disks, memory chips, read-only memory ("ROM"), random-access memory ("RAM"), an ASIC, a configured processor, optical storage, or any other medium from which a computer processor can read instructions.

Figure 6:
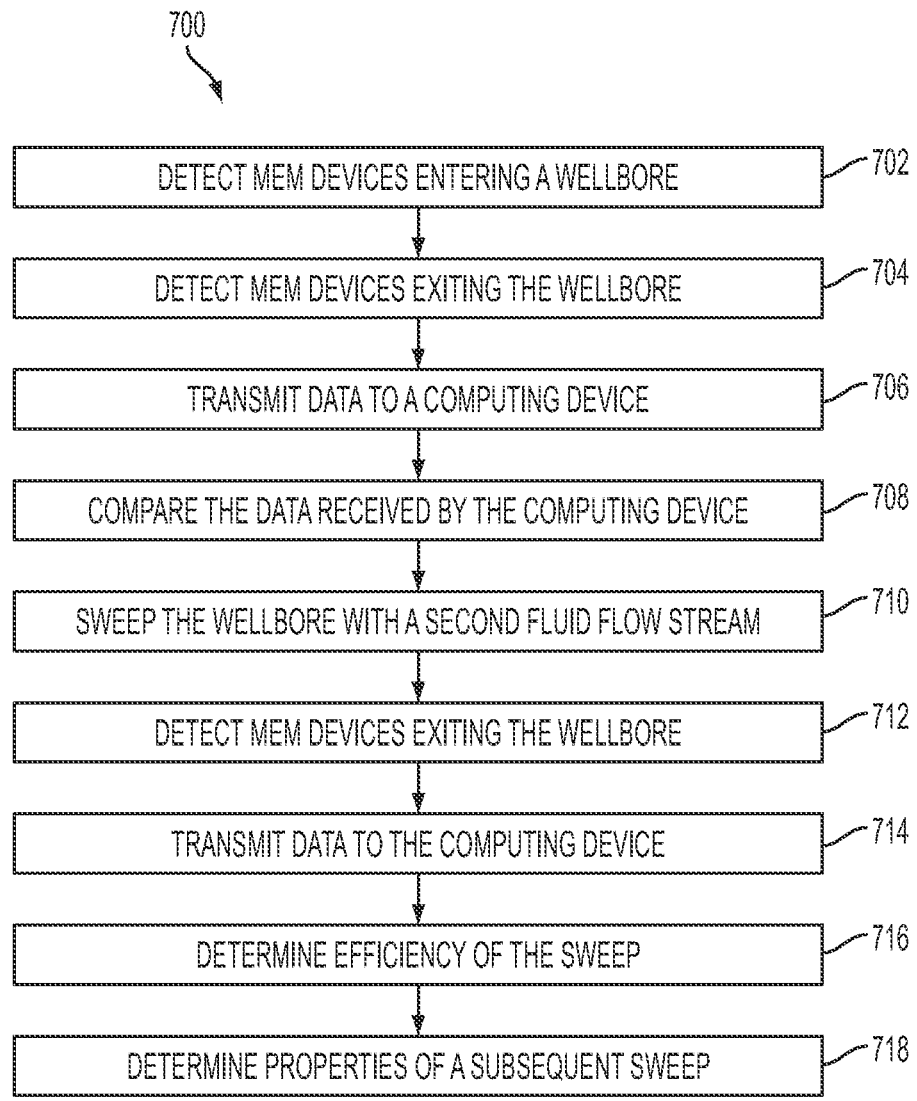
FIG. 6 is a flow chart showing a process for monitoring removal of MEM devices from a wellbore according to one example of the present disclosure.

FIG. 6 is a flow chart of an example of a process 700 for monitoring removal of MEM devices from a wellbore according to one example of the present disclosure.

In block 702, MEM devices entering a wellbore are detected. In some examples, a first MEM reader may detect MEM devices in a first fluid flow stream for a wellbore prior to a fluid flow input for the wellbore.

The MEM devices may be of various sizes, shapes, and densities and may represent non-desirable solids in the wellbore. The MEM devices may be disposable in the first fluid flow stream for a wellbore. The MEM devices may be disposable in the first fluid flow stream at any point in the first fluid flow stream prior to the first fluid flow stream entering a fluid flow input for a wellbore. The MEM devices may be disposable in the first fluid flow stream in any manner, including without limitation, through manual disposal or through automated disposal (e.g., by an apparatus, device, machine, or the like).

The first MEM reader may detect an amount and types of MEM devices in the first fluid flow stream prior to the fluid flow input for the wellbore through a communication link. In some examples, the communication link may be any link that facilitates communication between the individual MEM devices in the first fluid flow stream prior to the fluid flow input and the first MEM reader. The communication link may be wireless and can include wireless interfaces.

In some examples, identification information for each MEM device may be stored on a microchip on the MEM device. The first MEM reader may detect the identification information for each MEM device in the first fluid flow stream prior to the fluid flow input for the wellbore through the communication link.

In another example, the first MEM reader may detect an amount and types of MEM devices in the first fluid flow stream prior to the fluid flow input through electromagnetic fields and energy. For example, the MEM devices may be devices with RFID tags. The first MEM reader may be an RFID tag reader. Identification data may be stored within a microchip on the MEM devices. The MEM devices may transmit signals, through an electromagnetic field, to the first MEM reader. The first MEM reader may detect the MEM devices in the first fluid flow stream prior to the fluid flow input by detecting the signals and interpreting the identification data stored on the MEM devices.

The first MEM reader may also detect individual MEM devices and store data that may be representative of a distribution of the amount and types of MEM devices of different sizes, shapes, and densities in the first fluid flow stream prior to the fluid flow input.

In other examples, any reader for detecting or sensing MEM devices may detect the MEM devices entering the wellbore.

In block 704, MEM devices exiting a wellbore are detected. In some examples, a second MEM reader may detect MEM devices in a fluid flow stream subsequent to a fluid flow output for the wellbore.

The second MEM reader may detect an amount and types for MEM devices in the first fluid flow stream subsequent to a fluid flow output for the wellbore. The second MEM reader may detect the identification information for each MEM device in the first fluid flow stream subsequent to the fluid flow output through a communication link configured substantially the same as the communication link described above. The second MEM reader may also detect an amount and types of MEM devices in the first fluid flow stream subsequent to the fluid flow output through electromagnetic fields and energy configured substantially the same as the electromagnetic fields and energy described above.

In some examples, the second MEM reader may detect individual MEM devices and store data that may be representative of a distribution of the amount and types of MEM devices of different sizes, shapes, and densities in the first fluid flow stream subsequent to the fluid flow output.

In other examples, any reader for detecting or sensing MEM devices may detect the MEM devices exiting the wellbore.

In block 706, data is transmitted to a computing device. In some examples, a first MEM reader may transmit data to a computing device. The data may represent the amount and types of MEM devices in the first fluid flow stream prior to the fluid flow input for the wellbore. The first MEM reader may transmit other data that represents a distribution of the amount and types of MEM devices of different sizes, shapes, and densities in the first fluid flow stream prior to the fluid flow input.

A second MEM reader may also transmit data to the computing device. The data may represent the amount and types of MEM devices in the first fluid flow stream subsequent to the fluid flow output for the wellbore. The second MEM reader may transmit other data that represents a distribution of the amount and types of MEM devices of different sizes, shapes, and densities in the first fluid flow stream subsequent to the fluid flow output.

In block 708, the data transmitted to the computing device is compared. In some examples, the computing device may compare the data received from the first MEM reader and the second MEM reader. The computing device may compare the amount and types of MEM devices in the first fluid flow stream prior to the fluid flow input and the amount and types of MEM devices in the first fluid flow stream subsequent to the fluid flow output. The computing device may also compare the data received from the first MEM reader and the second MEM reader to determine the amount and types of MEM devices remaining in the wellbore after the first fluid flow stream exits the wellbore.

In block 710, the wellbore is swept with a second fluid flow stream. In some examples a second fluid flow stream may be disposed in the wellbore for sweeping the wellbore. The second fluid flow stream may be a sweep. The second fluid flow stream may be disposed in the wellbore for sweeping at least a subset of the MEM devices remaining in the wellbore after the first fluid flow stream exits the wellbore.

In block 712, MEM devices exiting the wellbore are detected. In some examples, the second MEM reader may detect MEM devices in the second fluid flow stream subsequent to the fluid flow output for the wellbore.

The second MEM reader may detect an amount and types of MEM devices in the second fluid flow stream subsequent to a fluid flow output for the wellbore. The second MEM reader may detect the identification information for each MEM device in the second fluid flow stream subsequent to the fluid flow output through a communication link configured substantially the same as the communication link described above. The second MEM reader may also detect an amount and types of MEM devices in the second fluid flow stream subsequent to the fluid flow output through electromagnetic fields and energy configured substantially the same as the electromagnetic fields and energy described above.

In some examples, the second MEM reader may detect individual MEM devices and store data that may be representative of a distribution of the amount and types of MEM devices of different sizes, shapes, and densities in the second fluid flow stream subsequent to the fluid flow output.

In other examples, any reader for detecting or sensing MEM devices may detect the MEM devices in the second fluid flow stream exiting the wellbore.

In block 714, data is transmitted to the computing device. In some examples, the second MEM reader may transmit data to the computing device. The data may represent the amount and types of MEM devices in the second fluid flow stream subsequent to the fluid flow output for the wellbore. The second MEM reader may transmit other data that represents a distribution of the amount and types of MEM devices of different sizes, shapes, and densities in the second fluid flow stream subsequent to the fluid flow output.

In block 716, the efficiency of the sweep is determined. In some examples, the computing device determines the efficiency of using the second fluid flow stream to sweep the wellbore.

The computing device may determine the efficiency of using the second fluid flow stream by determining an amount and types of MEM devices remaining in the wellbore after the second fluid flow stream exits the wellbore. The computing device may also determine the efficiency of using the second fluid flow stream by determining an amount and types of MEM devices removed from the wellbore by the second fluid flow stream.

The computing device may also determine the efficiency of using the second fluid flow stream by determining an amount and types of MEM devices of a shape, size, or density, representative of non-desirable solids of the same size, shape, or density remaining in the wellbore after the second fluid flow stream exits the wellbore.

The computing device may also determine the efficiency of using the second fluid flow stream by determining an amount of MEM devices of a shape, size, or density, representative of non-desirable solids of the same size, shape, or density removed from the wellbore by the second fluid flow stream.

In other examples, the computing device may determine the efficiency of using the second fluid flow stream by comparing the amount and types of MEM devices of different sizes, shapes, and densities removed from the wellbore by the second fluid flow stream to a threshold of expected efficiency for using the second fluid flow stream to sweep MEM devices from the wellbore.

In some examples, the process 700 for monitoring removal of MEM devices from a wellbore further includes, in block 718, the computing device determining properties of a subsequent sweep. The computing device may determine properties of a subsequent fluid flow stream disposable in the well bore for removing at least a subset of the amount and types of MEM devices remaining in the wellbore after the second fluid flow stream exits the wellbore. The computing device may compare the amount and types of MEM devices remaining in the wellbore after the first fluid flow stream exits the wellbore and the amount and types of MEM devices in the second fluid flow stream subsequent to the fluid flow output to determine the properties of the subsequent fluid flow stream. The computing device may also analyze the amount and types of MEM devices of different shapes, sizes, and densities remaining in the wellbore after the second fluid flow exits the wellbore to determine the properties of the subsequent fluid.

The computing device may determine properties of the subsequent fluid flow stream such as viscosity, density, or volume of the subsequent fluid flow stream.

Various types of systems can be used for monitoring removal of MEM devices from a wellbore to assess efficiency of using a fluid for wellbore cleaning. The following are examples.

Example #1

A method can include detecting MEM devices of different sizes, shapes, and densities in a first fluid flow stream from a wellbore to determine an amount and types of MEM devices that remain in the wellbore. The MEM devices can be representative of non-desirable solids in the wellbore. The method can also include detecting the MEM devices in a second fluid flow stream from the wellbore to determine the amount and types of MEM devices removed from the wellbore by the second fluid flow stream. The second fluid flow stream can be injected into the wellbore subsequent to detecting the MEM devices in the first fluid flow stream. The method can further include transmitting data about the amount and types of MEM devices removed from the wellbore by the second fluid flow stream to a computing device for determining sweep efficiency of the second fluid flow stream.

Example #2

The method of Example #1 may feature detecting the amount and types of MEM devices in the first fluid flow stream prior to the first fluid flow stream being injected into the wellbore to determine the amount and types of MEM devices that remain in the wellbore from the first fluid flow stream.

Example #3

The method of Example #2 may feature detecting, by a first MEM reader, the amount and types of MEM devices in the first fluid flow stream being injected into the wellbore. The method may also feature detecting, by a second MEM reader, the MEM devices in the first fluid flow stream from the wellbore.

Example #4

The method of any of Examples #1-3 may feature determining the sweep efficiency of the second fluid flow stream including outputting data to determine a change in a property of fluid used in a further fluid flow stream subsequently injected into the wellbore.

Example #5

The method of any of Examples #1-4 may feature determining the sweep efficiency of the second fluid flow stream including comparing the amount and types of MEM devices removed from the wellbore by the second fluid flow stream to the amount and types of MEM devices expected to be removed from the wellbore by the second fluid flow stream.

Example #6

The method of any of Examples #1-5 may feature generating a distribution of the types of MEM devices removed from the wellbore by the second fluid flow stream. The distribution can include a number of MEM devices per type of MEM device removed from the wellbore. The method may also feature using the distribution to determine a sweep efficiency rating for each type of MEM device represented in the distribution.

Example #7

A non-transitory computer-readable storage medium having program code that is executable by a processing device to cause a computing device to perform operations. The operations can include determining an amount and types of MEM devices of different sizes, shapes, and densities remaining in a wellbore after a first fluid flow stream is injected into the wellbore based on data detected by a MEM reader. The MEM devices can be representative of non-desirable solids in the wellbore. The operations can also include determining the amount and types of MEM devices among the MEM devices remaining in the wellbore that were removed from the wellbore by a second fluid flow stream injected after the first fluid flow stream based on data detected by the MEM reader. The operations can further include determining sweep efficiency of the second fluid flow stream using the amount and types of MEM devices removed from the wellbore.

Example #8

The storage medium of Example #7 may feature the MEM reader including a first MEM reader and a second MEM reader.

Example #9

The storage medium of any of Examples #7-8 may feature the operation of determining the amount and types of MEM devices remaining in the wellbore after the first fluid flow stream is injected further including operations for comparing data received from the MEM reader. The data can represent the amount and types of MEM devices in the first fluid flow stream prior to the first fluid flow stream being injected into the wellbore and the amount and types of MEM devices returning from the wellbore in the first fluid flow stream.

Example #10

The storage medium of any of Examples #7-9 may feature the operation of determining the amount and types of MEM devices removed from the wellbore by the second fluid flow stream further including operations for comparing data received from the MEM reader. The data can represent the amount and types of MEM devices remaining in the wellbore after the first fluid flow stream is injected and the amount and types of MEM devices returning from the wellbore in the second fluid flow stream.

Example #11

The storage medium of any of Examples #7-10 may feature the operation of determining the sweep efficiency of the second fluid flow stream further including operations for comparing the amount and types of MEM devices removed from the wellbore by the second fluid flow stream to the amount and types of MEM devices expected to be removed from the wellbore by the second fluid flow stream.

Example #12

The storage medium of any of Examples #7-11 may feature the operation of determining sweep efficiency of the second fluid flow stream further including operations for determining a sweep efficiency rating for each type of MEM device removed from the wellbore by the second fluid flow stream.

Example #13

The storage medium of Examples #12 may feature the operation of determining the sweep efficiency rating for each type of MEM device further including operations for generating a distribution of an amount of each type of MEM device removed from the wellbore.

EXAMPLES #14

The storage medium of any of Examples #12-13 may feature the operation of determining the sweep efficiency rating for each type of MEM device removed further including operations comparing the distribution of the amount of each type of MEM device removed from the wellbore by the second fluid flow stream to an amount of each type of MEM device expected to be removed from the wellbore by the second fluid flow stream.

Example #15

A system can use a first MEM reader and a second MEM reader. The first MEM reader can be positioned near a fluid flow stream injected into a wellbore for detecting an amount and types of MEM devices of different sizes, shapes, and densities in the first fluid flow stream. The second MEM reader can be positioned near (i) the first fluid flow stream from the wellbore for detecting any MEM devices returning from the wellbore in the first fluid flow stream and (ii) a second fluid flow stream from the wellbore for detecting the amount and types of MEM devices that remained in the wellbore from the first fluid flow stream and removed by the second fluid flow stream. The system can further include a processing device communicatively coupled with the first MEM reader and the second MEM reader for determining sweep efficiency of the second fluid flow stream using data from the second MEM reader. The data from the second MEM reader can represent the amount and types of MEM devices that remained in the wellbore from the first fluid flow stream and the amount and types of MEM devices removed by the second fluid flow stream.

Example #16

The system of Example #15 may feature the processing device being communicatively coupled to the first MEM reader for receiving data for determining the amount and types of MEM devices that remained in the wellbore from the first fluid flow stream. The data can represent an amount and types of MEM devices in the first fluid flow stream prior to the first fluid flow stream being injected into the wellbore.

Example #17

The system of any of Examples #15-16 may feature the processing module having machine-readable code for determining the sweep efficiency of the second fluid flow stream by comparing the amount and types of MEM devices removed by the second fluid flow stream to the amount and types of MEM devices expected to be removed from the wellbore by the second fluid flow stream.

Example #18

The system of any of Examples #15-17 may feature the processing module having machine-readable code for determining a sweep efficiency rating for each type of MEM device removed from the wellbore by the second fluid flow stream by generating a distribution representing the amount of each type of MEM device removed from the wellbore.

Example #19

The system of Example #18 may feature the processing module having machine-readable code for determining the sweep efficiency rating by comparing the amount of each type of MEM device removed from the wellbore by the second fluid flow stream to an amount of each type of MEM device expected to be removed from the wellbore by the second fluid flow stream.

Example #20

The system of any of Examples #15-19 may feature the processing module having machine-readable code for outputting data to determine a change in a property of fluid used in a further fluid flow stream subsequently injected into the wellbore.

The foregoing description of certain examples, including illustrated examples, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure.

What is claimed is:

1. A method comprising:
   detecting micro-electro-mechanical ("MEM") devices of different sizes, shapes, and densities in a first fluid flow stream from a wellbore to determine an amount and types of MEM devices that remain in the wellbore, the MEM devices representing non-desirable solids in the wellbore;
   detecting the MEM devices in a second fluid flow stream from the wellbore to determine the amount and types of MEM devices removed from the wellbore by the second fluid flow stream, the second fluid flow stream being injected subsequent to detecting the MEM devices in the first fluid flow stream; and
   transmitting data about the amount and types of MEM devices removed from the wellbore by the second fluid flow stream to a computing device for determining a sweep efficiency of the second fluid flow stream.

2. The method of claim 1, further comprising:
   detecting the amount and types of MEM devices in the first fluid flow stream prior to the first fluid flow stream being injected into the wellbore to determine the amount and types of MEM devices that remain in the wellbore from the first fluid flow stream.

3. The method of claim 2, wherein detecting the amount and types of MEM devices in the first fluid flow stream prior to the first fluid flow stream being injected into the wellbore includes using a first MEM reader,
   wherein detecting the MEM devices in the first fluid flow stream from a wellbore includes using a second MEM reader.

4. The method of claim 1, wherein determining the sweep efficiency of the second fluid flow stream includes outputting data to determine a change in a property of fluid used in a further fluid flow stream subsequently injected into the wellbore.

5. The method of claim 1, wherein determining the sweep efficiency of the second fluid flow stream includes comparing the amount and types of MEM devices removed from the wellbore by the second fluid flow stream to the amount and types of MEM devices expected to be removed from the wellbore by the second fluid flow stream.

6. The method of claim 1, wherein determining the sweep efficiency of the second fluid flow stream includes:
   generating a distribution of the types of MEM devices removed from the wellbore by the second fluid flow stream, the distribution including a number of MEM devices per type of MEM device removed from the wellbore;
   determining a sweep efficiency rating for each type of MEM device represented in the distribution.

7. A non-transitory computer-readable storage medium having program code that is executable by a processor device to cause a computing device to perform operations, the operations comprising:
   determining an amount and types of micro-electro-mechanical ("MEM") devices of different sizes, shapes, and densities remaining in a wellbore after a first fluid flow stream is injected into the wellbore based on data detected by a MEM reader, wherein the MEM devices are representative of non-desirable solids in the wellbore;
   determining the amount and types of MEM devices among the MEM devices remaining in the wellbore that were removed from the wellbore by a second fluid flow stream injected subsequent to the first fluid flow stream based on data detected by the MEM reader; and
   determining a sweep efficiency of the second fluid flow stream using the amount and types of MEM devices removed from the wellbore.

8. The non-transitory computer-readable storage medium of claim 7, wherein the MEM reader includes a first MEM reader and a second MEM reader.

9. The non-transitory computer-readable storage medium of claim 7, wherein the operation of determining the amount and types of MEM devices remaining in the wellbore after the first fluid flow stream is injected includes:
comparing data received from the MEM reader, the data representing the amount and types of MEM devices in the first fluid flow stream prior to the first fluid flow stream being injected into the wellbore and the amount and types of MEM devices returning from the wellbore in the first fluid flow stream.

10. The non-transitory computer-readable storage medium of claim 7, wherein the operation of determining the amount and types of MEM devices removed from the wellbore by the second fluid flow stream includes:
comparing data received from the MEM reader, the data representing the amount and types of MEM devices remaining in the wellbore after the first fluid flow stream is injected and the amount and types of MEM devices returning from the wellbore in the second fluid flow stream.

11. The non-transitory computer-readable storage medium of claim 7, wherein the operation of determining the sweep efficiency of the second fluid flow stream includes:
comparing the amount and types of MEM devices removed from the wellbore by the second fluid flow stream to the amount and types of MEM devices expected to be removed from the wellbore by the second fluid flow stream.

12. The non-transitory computer-readable storage medium of claim 7, wherein the operation of determining sweep efficiency of the second fluid flow stream includes:
determining a sweep efficiency rating for each type of MEM device removed from the wellbore by the second fluid flow stream.

13. The non-transitory computer-readable storage medium of claim 12, wherein the operation of determining the sweep efficiency rating for each type of MEM device removed includes:
generating a distribution of an amount of each type of MEM device removed from the wellbore.

14. The non-transitory computer-readable storage medium of claim 13, wherein the operation of determining the sweep efficiency rating for each type of MEM device removed further includes:
comparing the distribution of the amount of each type of MEM device removed from the wellbore by the second fluid flow stream to an amount of each type of MEM device expected to be removed from the wellbore by the second fluid flow stream.

15. A system comprising:
a first micro-electro-mechanical ("MEM") reader positionable with respect to a first fluid flow stream injected into a wellbore for detecting an amount and types MEM devices of different sizes, shapes, and densities in the first fluid flow stream being injected into the wellbore;
a second MEM reader positionable with respect to (i) the first fluid flow stream from the wellbore for detecting any MEM devices returning from the wellbore in the first fluid flow stream and (ii) a second fluid flow stream from the wellbore for detecting the amount and types of MEM devices that remained in the wellbore from the first fluid flow stream and removed by the second fluid flow stream;
a processing device communicatively coupled with the first MEM reader and the second MEM reader for determining a sweep efficiency of the second fluid flow stream using data from the second MEM reader that represents the amount and types of MEM devices that remained in the wellbore from the first fluid flow stream and removed by the second fluid flow stream.

16. The system of claim 15, wherein the processing device receives data from the first MEM reader for determining the amount and types of MEM devices that remained in the wellbore from the first fluid flow stream, the data representing an amount and types of MEM devices in the first fluid flow stream prior to the first fluid flow stream being injected into the wellbore.

17. The system of claim 15, wherein the processing module comprises machine readable code for determining the sweep efficiency of the second fluid flow stream by comparing the amount and types of MEM devices removed by the second fluid flow stream to the amount and types of MEM devices expected to be removed from the wellbore by the second fluid flow stream.

18. The system of claim 15, wherein the processing module comprises machine readable code for determining a sweep efficiency rating for each type of MEM device removed from the wellbore by the second fluid flow stream by generating a distribution representing the amount of each type of MEM device removed from the wellbore.

19. The system of claim 18, wherein the processing module comprises machine readable code for determining the sweep efficiency rating by comparing the amount of each type of MEM device removed from the wellbore by the second fluid flow stream to an amount of each type of MEM device expected to be removed from the wellbore by the second fluid flow stream.

20. The system of claim 15, wherein the processing module comprises machine readable code for outputting data to determine a change in a property of fluid used in a further fluid flow stream subsequently injected into the wellbore.

* * * * *